United States Patent [19]

Chern et al.

[11] Patent Number: 5,932,584
[45] Date of Patent: Aug. 3, 1999

[54] OPTICALLY ACTIVE 2,3-DIHYDROIMIDAZO(1,2-C) QUINAZOLINE DERIVATIVES, THE PREPARATION AND ANTIHYPERTENSIVE USE THEREOF

[75] Inventors: Ji-Wang Chern; Alexander Gutcait; Hsiu-Wen Liu; Kuang-Chao Wang, all of Taipei, Taiwan

[73] Assignee: National Science Council, Taipei, Taiwan

[21] Appl. No.: 08/851,967

[22] Filed: May 6, 1997

[51] Int. Cl.[6] .................. A61K 31/505; C07D 487/04
[52] U.S. Cl. .............................. 514/267; 544/250
[58] Field of Search .............................. 544/250; 514/267

[56] References Cited

U.S. PATENT DOCUMENTS

| | | | |
|---|---|---|---|
| 5,340,814 | 8/1994 | Chern et al. | 514/267 |
| 5,371,080 | 12/1994 | Hansen et al. | 514/228.5 |
| 5,512,677 | 4/1996 | Chern et al. | 514/267 |

OTHER PUBLICATIONS

Maryam Zakerinia, Hady Davary and Gholam H. Hakimelahi, "The Syntheses of Purine and Pyrimidine Secoribo–nucleosides: Acyclo–uridine Derivative of Cyclophosphamide," Helvetica Chimica Acta, vol. 73, 1990, pp. 912–915.

R.A. Johnson, "Encyclopedia of Reagents for Organic Synthesis," 1995, vol. 4, pp. 2609–2613.

Jun–ichi Imagawa and Kazushige Sakai, "Further Evaluation of the Selectivity of a Novel Antihypertensive Agent, SGB–1534, for Peripheral $\alpha_1$–adrenoceptors in the Spinally Anesthetized Dog," European Journal of Pharmacology, 1986, pp. 257–264.

Ji–Wang Chern, Pao–Luh tao, Mao–Hsiung Yen, Guan–Yu Lu, Chia–Yang Shiau, Yue–Jun Lai, Su–Lan Chien and Chao–Han Chan, "Studies on Quinazolines, 5.1 2,3–Dihydroimidazo[1,2–c]Quinazoline Derivatives: A Novel Class of Potent and Selective $\alpha_1$–Adrenoceptor Antagonists and Antihypertensive Agents," J. Med. Chem. 1993, pp. 2196–2207.

Oyo Mitsunobu, "The Use of Diethyl Azodicarboxylate and Triphenylphosphine in Synthesis and Transformation of Natural Products," 1981, pp. 1–28.

Ji–Wang Chern, et al., Studies on Quinazolines. 6. Asymmetric Synthesis of (S)–(+)– and (R)–(–)–3–[[4–(2–Methoxyphenyl)piperazin–1–yl]methyl]–5–methylthio–2,3–dihydroimidazo[1,2–c]quinazolines; Tetrahedron: Asymmetry, vol. 7, No. 6, pp. 1641–1648, Jun. 1996.

*Primary Examiner*—Richard L. Raymond
*Attorney, Agent, or Firm*—Hitt Chwang & Gaines, P.C.

[57] ABSTRACT

This invention relates to novel optically active 3-substituted methyl-5-methylthio-2,3-dihydroimidazo[1,2-c]quinazoline (I) and 3-substituted methyl-2,3-dihydroimidazo[1,2-c]quinazolin-5(6H)-one (II). This invention also relates to the therapeutical use of these novel compounds

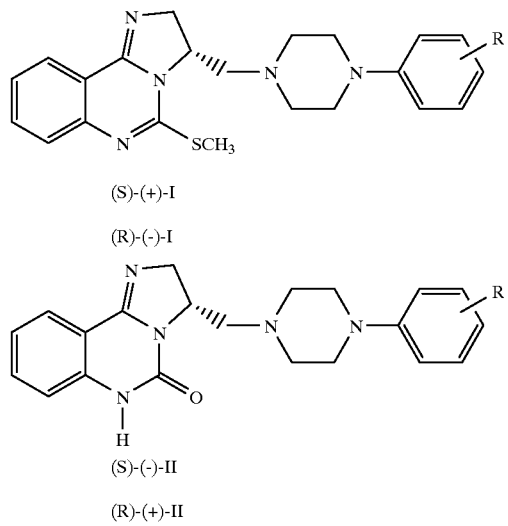

wherein: R is halogen, hydrogen, methoxy, trifluoromethyl, $C_1$–$C_4$ alkyl, nitro, acetyl, cyano or hydroxy group; or pharmaceutically acceptable salts thereof.

24 Claims, No Drawings

“5,932,584”

OPTICALLY ACTIVE 2,3-DIHYDROIMIDAZO(1,2-C) QUINAZOLINE DERIVATIVES, THE PREPARATION AND ANTIHYPERTENSIVE USE THEREOF

FIELD OF THE INVENTION

This invention relates to novel optically active 3-substituted methyl-5-methylthio-2,3-dihydroimidazo[1,2-c]quinazoline (I) and 3-substituted methyl-2,3-dihydroinidazo[1,2-c]quinazolin-5(6H)-one (II). This invention also relates to the therapeutical use of these novel compounds.

TECHNOLOGICAL BACKGROUND

The racemic compounds 3-substituted methyl-5-methylthio-2,3-dihydroimidazo[1,2-c]quinazoline (I) (Chern, J.-W. et. al. *J. Med. Chem.* 1993, 36, 2196–2207) and 3-substituted methyl-2,3-dihydroimidazo[1,2-c] quinazolin-5(6H)-one (II) have been recently synthesized as a conformational restricted analogs of 3-[[4-(2-methoxyphenyl)piperazin-1-yl]ethyl]quinazoline-2,4-dione, (SGB-1534, III) (Imagawa,J.; Sakai, K. *Eur. J. Pharmacol.* 1986, 131, 257–264) and have been shown to exhibit high potency and selectivity toward $\alpha_1$-adrenoreceptor. One of these compounds is currently undergoing intensive studies as an antihypertensive agent. The stereochemical requirements for biological activity remained to be clarified.

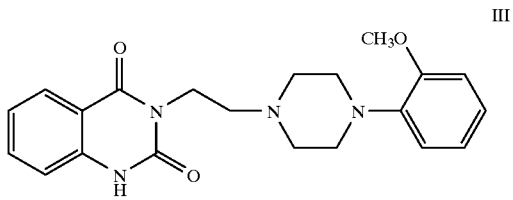

III

SUMMARY

This invention has demonstrated the ready availability of (R)-(+) and (S)-(–)-glycidol and their efficiency in the preparation of the enantiomers of compounds having general formulas I and II:

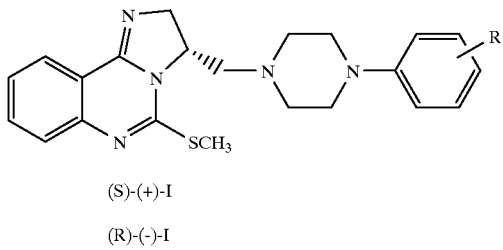

(S)-(+)-I
(R)-(–)-I

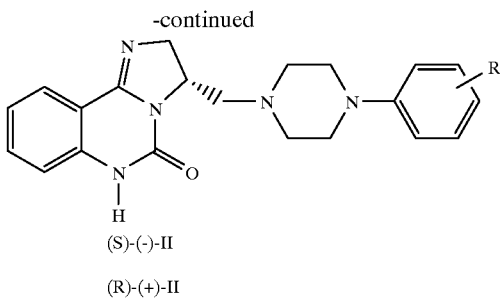

(S)-(–)-II
(R)-(+)-II wherein: R is halogen, hydrogen, methoxy, trifluoromethyl, $C_1$–$C_4$ alkyl, nitro, acetyl, cyano or hydroxy group.

The present invention also discloses processes for the preparation of the compounds having general formulas I and II.

The present invention further discloses pharmaceutical compositions for the treatments of hypertension and dysuria, which comprise a therapeutically effective amount of the compound of the formulas I or II or a pharamaceutically acceptable salt thereof, as an active ingredient, in admixture with a pharmaceutically acceptable carrier or diluent for the active ingredient.

The present further discloses a method for the treatment of hypertension and prostatauxe comprising administering a therapeutically effective amount of a compound of the formulas I or II to a subject suffering from high blood pressure.

DETAILED DESCRIPTION

The synthesis began with the condensation of glycidol (IV) with phthalimide under Mitsunobu reaction conditions (Mitsunobu, O. *Synthesis.* 1981, 1–28) in THF at room temperature and gave the 1,2-epoxy-3-phthaloylaminopropane (V) in 80–86% yield. Glycidol was reported (Johnson, R. A. In *Encyclopedia of Reagents for Organic Synthesis*; Paquette, L. A.; Eds.; Jon Willey & Sons, Inc.: New York, 1995; Vol. 4, pp. 2609–2613.) to be unstable and undergo self-condensation in the presence of traces of acids as catalyst in epoxide ring opening.

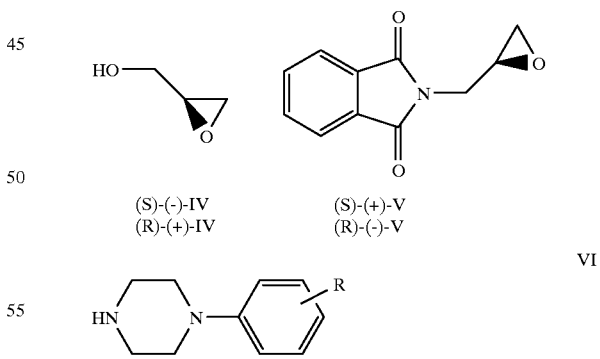

(S)-(–)-IV    (S)-(+)-V
(R)-(+)-IV    (R)-(–)-V

VI wherein: R is halogen, hydrogen, methoxy, trifluoromethyl, $C_1$–$C_4$ alkyl, nitro, acetyl, cyano or hydroxy group;

Thus, using freshly distilled glycidol is required to obtain pure compound V without intensive chromatographic purification. The yield was within the range of 73–83%. The condensation of epoxy derivative V with an equimolar amount of 4-(o-substituted phenyl)piperazines (VI) was performed at reflux in THF for 3 days and the yield of resulting 1-phthaloylamino-3-(substituted piperazin-1-yl)

propan-2-ols (VII) after column chromatography was 68–72%. However, when the reaction was carried out with an excess amount of piperazine derivative, the chromatographically pure compound VII was isolated in 73–83% yield by simply washing the crude product with ether to remove the excess piperazine.

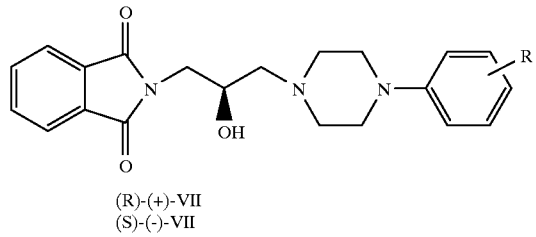

(R)-(+)-VII
(S)-(-)-VII

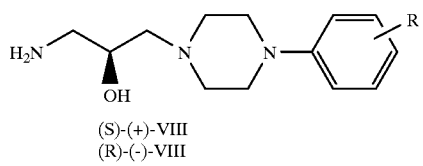

(S)-(+)-VIII
(R)-(-)-VIII wherein: R is halogen, hydrogen, methoxy, trifluoromethyl, $C_1$–$C_4$ alkyl, nitro, acetyl, cyano or hydroxy group;

The next step was conducted smoothly by treatment of compound VII with hydrazine hydrate in ethanolic solution at room temperature to furnish 1-amino-3-[4-(2-methoxyphenyl)piperazin-1-yl]propan-2-ol (VIII) as monohydrate with 86–94% yield. Compound VIII turned out to be soluble in water and the precipitated phthalic acid hydrazide was filtered off from the mixture.

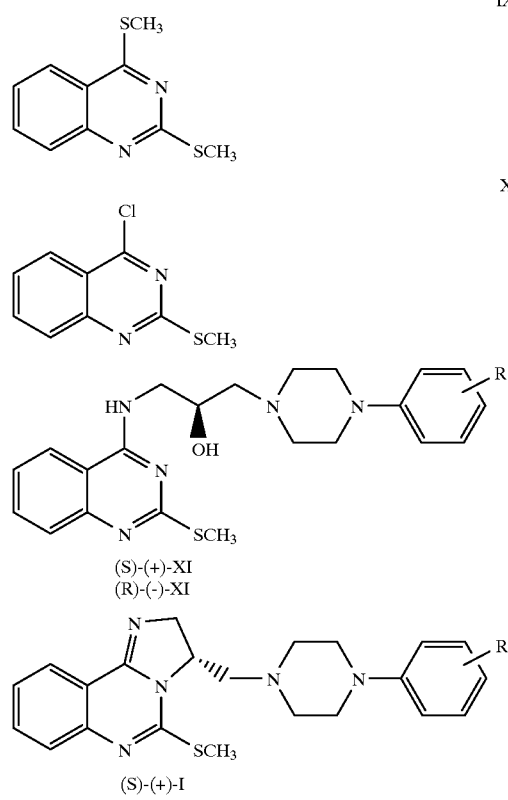

IX

X (S)-(+)-XI
(R)-(-)-XI (S)-(+)-I

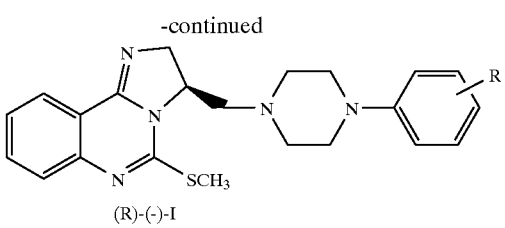

(R)-(-)-I

Aminoalcohol VIII was then allowed to react with 2,4-dimethylthioquinazoline (IX) in acetonitrile at reflux to give 4-[(3-(4-methoxyphenyl)piperazine-1-yl)propan-2-ol-1-yl] amino-2-methylthioquinazoline (XI). But the results were variable in the yields ranging from 24 to 56% and the reaction released notorious methylthiol. The possibility of synthesizing compound XI by using 4-chloro-2-methylthioquinazoline (X) was also investigated. Compound X was obtained in good yield (90–93%) starting from anthranilamide by heating with carbon disulfide in water-alcohol solution of potassium hydroxide to afford 2-mercaptoquinazolin-4-one (XII) in 91% yield. (Zakerinia, M. et. al. *Helv. Chim. Acta*. 1990, 73, 912–915) Compound XII was then methylated with methyl iodide to give 2-methylthioquinazolin-2-one (XIII) which was subsequently converted to 4-chloro-2-methylthioquinazoline (X) in high yield (90–93%) by treating with $POCl_3$, followed by precipitation with water from acetone solution. Compound X was reacted smoothly with amino alcohol VIII in the presence of triethylamine to give compound XI in 72% yield. The cyclization of XI to compound I was achieved by methanesulphonylchloride (MsCl) and triethylamine. The cyclization reaction proceeded in 12–17 hours to give compound I with 47–69% chemical yield after chromatographical purification. The addition of potassium carbonate to the reaction mixture to trap hydrogen chloride formed allowed to obtain a chromatographically pure compound I in 77% yield without column chromatography.

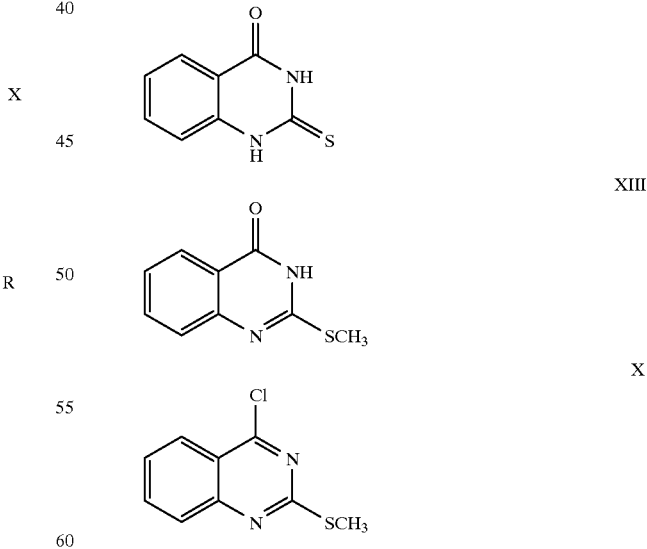

XII

XIII

X

It is of interest to note that the enantiomers of compound I had very good solubility in several solvents such as acetonitrile, isopropanol and ethanol when compare to racemic compound I which was crystallized from the above mentioned solvents. Thus, when the acetonitrile solutions of enantiomers (S)-I and (R)-I are mixed together by having one of them in excess amount, the racemic (RS)-I will precipitate immediately and quantitatively as a fine crystalline solid. However, only the one that is used in excess remained in filtrate solution. This would make it possible to obtain consistancy in enantiomeric purity of the synthesized compounds. Simple treatment of the sample with acetonitrile can be applied to separate the enantiomers (S)-I or (R)-I from the crystalline racemic (RS)-I by filtration. By HPLC analysis, the enantiomers of I obtained after evaporation of acetonitrile solution had more than 98.5% ee. The optical purity of starting materials influences only on the yield of pure enantiomers I. Treatment of (S)-(+)-I or (R)-(−)-I under acidic or basic condition led to the formation of (S)-(−)-II or (R)-(+)-II respectively.

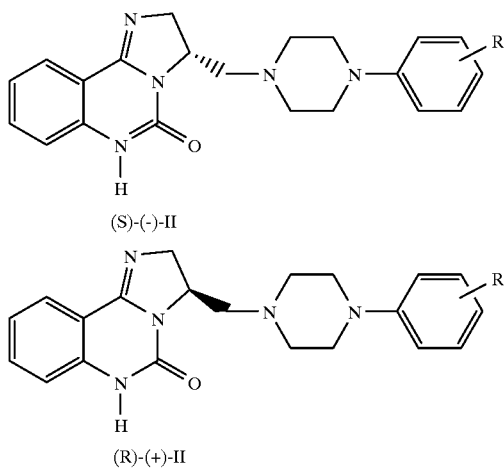

The homochiral compounds were subjected to a1-adrenoceptor binding affinity assay. The preliminary results illustrated that the affinity of enantiomer (S)-I to $\alpha_1$-adrenoceptor (Ki=1.88 nM) is 295-fold better than that of enantiomer (R)-I (Ki=554 nM), whereas, the racemic (RS)-I showed a Ki value of 3.55 nM. The (S)-(−)-II is the most potent with Ki=0.1 nM. The pharmacological activities of the compounds of the present invention are described in the following experiment. In this experiment, the test compounds used are as follows.

Methods of Binding Studies
1. Preparation of membranes for binding studies

Rat brain cortex membranes were prepared for [$^3$H] prazosin or [$^3$H] clonidine binding by homogenizing tissues in 0.32 M sucrose buffered with 50 mM Tris buffer (pH 7.4) in a tissue/buffer ratio of 1:10. After the removal of nuclei by centrifugation at 1000×g for 10 min, $P_2$ membranes were pelleted by centrifuging the supernatant at 22,000×g for 20 min. After two periods of centrifugation at 22,000×g and resuspension in fresh buffer, the membrane suspension (about 2 mg/ml protein) was ready for use.
2. Binding assays $\alpha_1$-Adrenergic receptor binding assays (in triplicate) were carried out with 0.2 nM [$^3$H] prazosin in a final volume of 1.0 ml of Tris buffer at pH 7.4 for 30 min at room temperature, using 10 mM phentolamine to determine nonspecific binding. The concentrations of synthetic compounds for competition binding were in the range of 0.1–200 nM. The concentrations of synthetic compounds for competition binding were in the range of 0.1–100 μM. After binding had reached equilibrium, incubations were terminated by collecting the membranes on Whatman GF/B filters; the filters were washed twice with 5 ml of 50 mM Tris buffer (pH 7.4) at 4° C. The amount of membrane protein used in each assay was in the range of 300–400 mg, as determined by the method of Lowry et al. The results are given in Table 1.

Materials

[$^3$H]prazosin (76.6 Ci/mmol) and [$^3$H]clonidine (47.0 Ci/mmol) were purchased from NEN. All other chemicals used were reagent grade and were purchased from Sigma (St. Louis, Mo.).

TABLE 1

| $\alpha_1$-Adrenergic Receptor Binding Affinities for Imidazo[1,2-c]quinazoline Derivatives | |
|---|---|
| Compounds | $\alpha_1$ Binding (Ki, nM) |
| Example 16 | 1.88 |
| Example 17 | 554 |
| Example 18 | 0.1 |
| Example 19 | 26 |

Preferred compounds are those prepared by the following Examples:

EXAMPLE 16
(S)-(+)-3-[(4-(2-methoxyphenyl)piperazin-1-yl]methyl-5-methylthio-2,3-dihydroimidazo[1,2-c]quinazoline EXAMPLE 17
(R)-(−)-3-[(4-(2-methoxyphenyl)piperazin-1-yl]methyl-5-methylthio-2,3-dihydroimidazo[1,2-c]quinazoline EXAMPLE 18
(S)-(−)-3-[(4-(2-methoxyphenyl)piperazin-1-yl]methyl-2,3-dihydroimidazo-[1,2-c]quinazolin-5(6H)-one.

EXAMPLE 19
(R)-(+)-3-[(4-(2-methoxyphenyl)piperazin-1-yl]methyl-2,3-dihydroimidazo-[1,2-c]quinazolin-5(6H)-one EXAMPLE 1
Preparation of 4-(2-methoxyphenyl)piperazine The mixture of 1-(2-methoxyphenyl) piperazine hydrochloride (6.86 g, 30 mmol), aq. NaOH (2.5N, 36 mL, 90 mmol) and chloroform (30 mL) was vigorously stirred for 0.5 h. Chloroform layer was separated and stirred with water (50 mL) for another 0.5 h. Chloroform layer after separation was filtrated through $Na_2SO_4$ (2 g) and evaporated in vacuo to dryness. The oil residue was dried in vacuo (2 mm Hg, 1 h, 80° C.) to give 5.50 g (95%) of 4-(2-methoxyphenyl) piperazine as slightly yellow oil. It was used in synthesises without further purification.

EXAMPLE 2
Preparation of (S)-(+)-1,2-epoxy-3-phthaloylaminopropane

To a stirred solution of phthalimide (1.93 g, 13.11 mmol) in dry THF (20 mL) was added triphenylphosphine (3.44 g, 13.11 mmol) followed by (S)-(+)-glycidol (1.12 g, 15.08 mmol) and diethyl azodicarboxylate (2.28 g, 13.11 mmol). The reaction mixture was stirred for 18 h at room temperature and the solvent was removed in vacuo. The residue was stirred with ether (50 mL) for 2 h and the precipitate was removed by filtration. The filtrate was evaporated in vacuo and the residue was purified by column chromatography (eluent: ethyl acetate/chloroform=1/10) to give 1.48 g (80%) of the title compound as colourless solid: mp 102–103° C.; $[\alpha]_D^{26}$ +9 (c 2.2, CHCl$_3$); $^1$H NMR (CDCl$_3$) δ 7.87–7.82 (m, 2H, Ar-H), 7.76–7.71 (m, 2H, ArH), 3.95 (dd, 1H, J=14.3, 5.1 Hz, CH$_2$O), 3.80 (dd, 1H, J=14.3 Hz, J=5.1 Hz, CH$_2$O), 3.25–3.20 (m, 1H, CHO), 2.78 (pseudo t, 1H, J=4.4 Hz, NCH$_2$), 2.68 (dd, 1H, J=4.80, 2.61 Hz, NCH$_2$); $^{13}$C NMR (CDCl$_3$) δ 168.56, 134.71, 132.50, 124.02, 49.65, 46.68, 40.22

EXAMPLE 3
Preparation of (R)-(−)-1,2-epoxy-3-phthaloylaminopropane

The title compound was obtained in 86% yield using a similar procedure which described in Example 2 as colourless solid: mp 102° C.; [α]$_D^{26}$ −9 (c 2.2, CHCl$_3$); $^1$H NMR (CDCl$_3$) δ 7.90–7.84 (m, 2H, ArH), 7.77–7.71 (m, 2H, ArH), 3.96 (dd, J=14.4, 5.0 Hz), 3.81 (dd, 1H, J=14.4, 5.0 Hz), 3.27–3.21 (m, 1H, CHO), 2.81 (dd, 1H, J=4.6, 4.1 Hz), 2.70 (dd, 1H, J=4.8, 2.5 Hz); $^{13}$C NMR (CDCl$_3$) δ 168.58, 134.73, 132.50, 124.03, 49.65, 46.70, 40.23; MS m/z 203 (M$^+$). Anal. Calc. for C$_{11}$H$_9$NO$_3$: C 64.92; H 4.46; N 6.89. Found C 64.70; H 4.37; N 6.92.

EXAMPLE 4
Preparation of (R)-(+)-5-(1-phthaloylamino)-3-[4-(2-methoxyphenyl)]piperazin-1-yl]propan-2-ol Method 1 To a stirred solution of 4-(2-methoxyphenyl) piperazine (5.07 g, 26.37 mmol) in dry THF (50 mL) was added (S)-(+)-1,2-epoxy-3-phthaloylaminopropane (4.15 g, 20.42 mmol) and the mixture was heated under reflux for 3 days. The solvent was removed in vacuo and the residue was purified by column chromatography (eluent: methanol/ethyl acetate/dichloromethane=1/1/20 ) to give 5.47 g (68%) of the title compound as colorless solid: mp 155–157° C.; [α]$_D^{26}$ +8 (c 0.5, CHCl$_3$); $^1$H NMR (CDCl$_3$) δ 7.88–7.83 (m, 2H, ArH), 7.75–7.71 (m, 2H, ArH), 7.02–6.90 (m, 4H, ArH), 4.12–4.06 (m, 1H, CH), 3.85–3.77 (m, 5H, CH$_3$, CH$_2$), 3.06 (br s, 4H, NCH$_2$), 2.87–2.44 (m, 7H, NCH$_2$, CH$_2$, OH); $^{13}$C NMR (CDCl$_3$) δ 169.13, 152.78, 141.65, 134,58, 132.62, 123.94, 123.59, 121.53, 118.76, 111.74, 65.47, 62.13, 55.92, 54.02, 51.28, 42.61; MS m/z 395 (M$^+$). Anal. Calcd. for C$_{22}$H$_{25}$N$_3$O$_4$: C 66.82; H 6.37; N 10.60. Found C 66.86; H 6.34; N 10.43.

EXAMPLE 5
Preparation of (S)-(−)-5-(1-Phthaloylamino)-3-[4-(2-methoxyphenyl)]piperazin-1-yl]-propan-2-ol The title compound was obtained in 72% yield from using (R)-(−)-1,2-epoxy-3-phthaloylaminopropane by a similar procedure which described in Example 4: [α]$_D^{28}$ −8 (c 0.3, CHCl$_3$); $^1$H NMR (CDCl$_3$) δ 7.90–7.84 (m, 2H, ArH), 7.75–7.71 (m, 2H, ArH), 7.03–6.84 (m, 4H, ArH), 4.12–4.05 (m, 1H, CH), 3.79–3.72 (m, 2H, CH$_2$), 3.86 (s, 3H, CH$_3$), 3.06 (br s, 4H, NCH$_2$), 2.87–2.44 (m, 7H, NCH$_2$, CH$_2$, OH); $^{13}$C NMR (CDCl$_3$) δ 169.13, 152.78, 141.63, 134,59 132.62, 123.94, 123.61, 121.53, 118.76, 111.71, 65.46 62.13, 55.92, 54.13, 51.26, 42.61; MS m/z 395 (M$^+$). Anal. Calcd for C$_{22}$H$_{25}$N$_3$O$_4$.0.5H$_2$O: C 65.33; H 6.48; N10.39. Found C 65.05; H 6.31; N 10.24.

EXAMPLE 6
Preparation of (S)-(−)-5-(1-phthaloylamino)-3-[4-(2-methoxyphenyl)]piperazin-1-yl]-propan-2-ol Method 2 To a stirred solution of 4-(2-methoxyphenyl) piperazine (6.03 g, 31.0 mmol) in dry THF (150 mL) was added (R)-(−)-1,2-epoxy-3-phthaloylaminopropane (5.49 g, 27.0 mmol) and the mixture was heated under reflux for 3 days. The solvent was removed in vacuo and the residue was stirred in ether (200 mL) for 3 h. The precipitate was collected by filtration and washed with ether (50 mL) to afford 7.81 g (73%) of the title compound.

EXAMPLE 7
Preparation of (R)-(+)-5-(1-phthaloylamino)-3-[4-(2-methoxyphenyl)]piperazin-1-yl]propan-2-ol The title compound was obtained in 83% yield using (S)-(+)-1,2-epoxy-3-phthaloylaminopropane by a similar procedure which described in Example 6.

EXAMPLE 8
Preparation of (S)-(+)-1-amino-3-(4-(2-methoxyphenyl) piperazin-1-yl)propan-2-ol To a stirred suspension of (R)-(+)-5-(1-phthaloylamino)-3-[4-(2-methoxyphenyl)]piperazin-1-yl]propan-2-ol (7.0 g, 17.7 mmol) in ethanol (180 mL) was added hydrazine monohydrate (4.31 mL, 88.7 mmol) and the solution was stirred at 25° C. for 12 h. The mixture was filtered and the filtrate was evaporated to dryness. The residue was dissolved in water (125 mL) and the solution was extracted with CHCl$_3$ (2×125 mL). The extracts were filtered through Na$_2$SO$_4$ (20 g) and evaporated to dryness to give slightly yellow oil which was crystallized after stirring with ether (60 mL) to afford 4.03 g (86%) of the title compound as white crystalline solid: mp 76–80° C.; [α]$_D^{26}$ +22.3 (c 2.1, CHCl$_3$); $^1$H NMR (CDCl$_3$) δ 7.03–6.85 (m, 4H, ArH), 3.86 (s, 3H, OCH$_3$), 3.72–3.77 (m, 1H, CHOH), 2.87–2.80 (m, 3H), 2.68–2.61 (m, 3H), 2.46–2.40 (m, 2H), 2.23 (br. s, 3H, NH$_2$, OH, exchangeable with D$_2$O). Anal. Calcd. for C$_{14}$H$_{23}$N$_3$O$_2$.H$_2$O: C 59.34; H 8.89; N 14.82. Found C 59.50; H 9.06; N 14.83.

EXAMPLE 9
Preparation of (R)-(−)-1-amino-3-(4-(2-methoxyphenyl) piperazin-1-yl)propan-2-ol The title compound was obtained in 94% yield using (S)-(−)-5-(1-phthaloylamino)-3-[4-(2-methoxyphenyl)] piperazin-1-yl]propan-2-ol as starting material by a similar procedure which described in Example 8: [α]$_D^{26}$ −22.3 (c 1.9, CHCl$_3$); $^1$H NMR (CDCl$_3$) δ 7.04–6.85 (m, 4H, ArH), 3.86 (s, 3H OCH$_3$), 3.78–3.73 (m, 1H, CHOH), 2.90–2.81 (m, 3H), 2.68–2.60 (m, 3H), 2.50–2.36 (m, 2H), 2.30 (br. s, 3H, NH$_2$, OH, exchangeable with D$_2$O); $^{13}$C NMR (CDCl$_3$) δ 152.79, 141.70, 123.60, 121.54, 118.76, 111.71, 68.37, 62.07, 55.92, 54.09, 51.29, 45.41; MS m/z 265 (M$^+$). Anal. Calcd. for C$_{14}$H$_{23}$N$_3$O$_2$.0.5H$_2$O: C 61.29; H 8.82; N 15.32. Found C 61.41; H 8.83; N 15.11.

EXAMPLE 10
Preparation of (S)-(+)-4-[(3-(4-methoxyphenyl)piperazine-1-yl)propan-2-ol-1-yl]amino-2-methylthioquinazoline The solution of 2,4-dimethylthioquinazoline (0.7 g, 3.15 mmol) and (S)-(+)-1-amino-3-(4-(2-methoxyphenyl) piperazin-1-yl)propan-2-ol (0.76 g, 2.86 mmol) in acetonitrile (25 mL) was heated under reflux for 4 days. The solvent was evaporated in vacuo and the residue was purified by column chromatography (ethyl acetate as eluent) to give 0.41 g (33%) of the title compound as slightly yellow solid: mp>78° C. dec.; [α]$_D^{28}$ +6 (c 2.9, CHCl$_3$); $^1$H NMR (CDCl$_3$+D$_2$O) δ 7.70–7.63 (m, 3H, ArH), 7.35–7.29 (m, 1H, ArH), 7.04–6.86 (m, 4H, ArH), 4.09–4.06 (m, 1H, CHOH), 3.95 (dd, 1H, J=3.30, 13.75 Hz, CH$_2$), 3.87 (s, 3H, OCH$_3$), 3.63 (dd, 1H, J=6.0, 13.9 Hz, CH$_2$), 3.11 (br s, 4H, NCH$_2$), 2.88–2.84 (m, 2H, NCH$_2$), 2.67–2.51 (m, 7H, SCH$_3$, NCH$_2$, CH$_2$); $^{13}$C NMR (CDCl$_3$) δ 159.43, 152.83, 150.89, 141.59, 133.44, 127.66, 125.03, 123.71, 121.56, 118.75, 113.36, 111.81, 66.17, 61.92, 55.96, 54.25, 54.12, 51.25, 45.14, 14.69. Anal. Calcd. for C$_{23}$H$_{29}$N$_5$O$_2$S.0.5H$_2$O: C 61.58 H 6.74; N 15.61. Found C 61.44; H 6.72; N 15.68.

EXAMPLE 11
Preparation of (R)-(-)-4-[(3-(4-methoxyphenyl)piperazine-1-yl)propan-2-ol-1-yl]amino-2-methylthioquinazoline The title compound was obtained in 72% yield using (R)-(-)-1-amino-3-(4-(2-methoxyphenyl)piperazin-1-yl) propan-2-ol as starting material by a similar procedure which described in Example 10: $[\alpha]_D^{28}$ −6 (c 2.4, CHCl$_3$); $^1$H NMR (CDCl$_3$) δ 7.70–7.66 (m, 3H, ArH), 7.35–7.30 (m, 1H, ArH), 7.05–7.00 (m, 1H, ArH), 7.05–6.86 (m, 3H, Ar-H), 6.46 (t, 1H, J=5.0 Hz, NH), 4.11–4.05 (m, 1H, CHOH), 3.95 (ddd, 1H, J=3.6, 5.3, 13.7 Hz, CH$_2$), 3.87 (s, 3H, OCH$_3$), 3.65 (ddd, 1H, J=5.4, 5.4, 13.7 Hz, CH$_2$), 3.11 (br s, 4H, NCH$_2$), 2.91–2.86 (m, 2H, NCH$_2$), 2.68–2.64 (m, 2H), 2.62 (s, 3H, SCH$_3$), 2.58–2.48 (m, 2H); $^{13}$C NMR (CDCl$_3$) δ 159.41, 152.82, 150.89, 141.59, 133.45, 127.67, 125.03, 123.71, 121.55, 118.74, 113.35, 111.78, 66.13, 61.90, 55.96, 54.12, 54.12, 51.25, 45.11, 14.71; MS m/z 439 (M$^+$) Anal. Calcd. for C$_{23}$H$_{29}$N$_5$O$_2$S.H$_2$O: C 60.37; H 6.39; N 15.30.Found C 60.51; H 6.57; N 15.21.

EXAMPLE 12
Preparation of 2-methylthioquinazolin-4(3H)-one

To a solution of 2-mercaptoquinazolin-4(3H)-one (4.45 g, 25 mmol) and NaOH (1.1 g, 27.5 mmol) in water (125 mL) was added methyl iodide (1.72 mL, 27.5 mmol) and the mixture was stirred at 25° C. for 3 h. The precipitate was collected by filtration, washed with water (3×20 mL) and dried in vacuum desiccator over silica gel for 24 h to give 3.66 g (73%) of the title compound as colorless solid: mp 224–225° C. An analytical sample was recrystallized from methanol-water: mp 225° C.; $^1$H NMR (CDCl$_3$) δ 11.25 (br s, 1H, NH), 8.27 (dd, 1H, J=1.25, 6.3 Hz, ArH), 7.62 (d, 1H, J=7.3 Hz), 7.44–7.38 (m, 1H, ArH), 2.70 (s, 3H, SCH$_3$); $^{13}$C NMR (CDCl$_3$) δ 163.73, 155.76, 149.77, 135.50, 127.30, 126.96, 126.40, 120.37, 13.97.

EXAMPLE 13
Preparation of 4-chloro-2-methylthioquinazoline

Method 1. The mixture of 2-methylthioquinazolin-4(3H)-one (1.92 g, 10 mmol) and POCl$_3$ (4.7 mL, 50 mmol) was stirred for 15 min at room temperature and the suspension was heated under reflux for 1.5 h. After cooling to the room temperature, the mixture was poured into a mixture of ice (40 g) and methylene chloride (20 mL) with vigorously stirring for 5 min. The organic layer was then separated and washed with 5% aq K$_2$CO$_3$ (2×20 mL). The organic layer was dried with Na$_2$SO$_4$ (3 g) and then was filtered through of 1 g silica gel. The filtrate was evaporated in vacuo to give 1.91 g (91%) of the title compound as colorless solid: mp 107–108° C.; $^1$H NMR (CDCl$_3$) δ 8.15–8.12 (m, 1H, ArH), 7.85–7.83 (m, 2H, ArH), 7.58–7.52 (m, 1H, ArH), 2.67 (s, 1H, SCH$_3$); $^{13}$C NMR (CDCl$_3$) δ 152.38, 135.79, 135.75, 127.72, 127.63, 127.58, 126.69, 126.64, 14.99. Anal. Calcd. for C$_8$H$_7$ClN$_2$S: C 48.37; H 3.55; N 14.10. Found C 48.32; H 3.60; N 14.04.

Method 2. When the reaction mixture was poured into ice with vigorously stirring, the precipitate was collected by filtration and washed with 5% aq. K$_2$CO$_3$ (2×50 mL), water (100 mL). The crude product was dissolved in acetone (100 mL) and reprecipitated with water (100 mL) to give 1.73 g (82%) of the title compound as colorless needles: mp 108–109° C.

Method 3. To a stirred suspension of 2-methylthioquinazolin-4(3H)-one (0.5 g, 2.60 mmol) and triphenylphosphine (0.82 g, 3.12 mmol) in dichloromethane was added carbon tetrachloride (2.5 mL) and the resulting suspension was stirred at 20–25° C. After 6 h, the reaction was completed (TLC) and filtrated through the column of silica gel (2.5×15 cm) using dichloromethane as eluent. The right fraction was collected and evaporated in vacuo. The residue was dissolved in acetone (10 mL) and reprecipitated with water (30 mL) to afford a white crystalline solid which was dried in vacuo over CaCl$_2$ to give 0.46 g (83%) of the title compound: mp 108° C.

EXAMPLE 14
Preparation of (S)-(+)-3-[(4-(2-methoxyphenyl)piperazin-1-yl]methyl-5-methylthio-2,3-dihydroimidazo[1,2-c] quinazoline To a solution of (S)-(+)-4-[(3-(4-methoxyphenyl) piperazine-1-yl)propan-2-ol-1-yl]amino-2-methylthio quinazoline (1.72 g, 3.9 mmol) in dry methylene chloride under an argon atmosphere at 0° C. was added triethylamine (2.73 mL, 19.6 mmol). The mixture was stirred for 15 min and methanesulfonylchloride (0.40 mL, 5.1 mmol) was added over the period of 30 min. The mixture was stirred at 0° C. for 1 h and at 25° C. for 7 h. Then it was diluted with methylene chloride (20 mL) and washed sequentially with water (50 mL), sat. aq. NaHCO$_3$ (20 mL) and water (20 mL). The organic layer was filtrated through Na$_2$SO$_4$ (2 g) and concentrated to afford crude product which was purified by flash chromatography using ethyl acetate as eluent. The residue that obtained after evaporation of solvent was stirred with acetonitrile (2 mL) for 1 h and the precipitate was collected to give 0.148 g (9.0%) of racemic product mp 172–173° C.; $[\alpha]_D^{26}$ +5.72 (c 0.278, CHCl$_3$), HPLC analysis indicated that the racemic mixture contained 55.7% of the title compound and 44.7% of (R)-(-)-3-[(4-(2-methoxyphenyl)piperazin-1-yl]methyl-5-methylthio-2,3-dihydroimidazo[1,2-c]quinazoline.

The filtrate was evaporated in vacuo and the residue was heated at 60–70° C. in vacuo (5 mm) to afford 1.13 g (69%, ee>98.5%) of the title compound as colorless solid foam: mp. 58–61° C. (softing), 62–63° C. (transparent); $[\alpha]_D^{26}$ +39.6 (c 4.7, CHCl$_3$); $^1$H NMR (CDCl$_3$) δ 7.96 (dd, J=1.4, 7.9 Hz, 1H, ArH), 7.52 (t, J=7.7 Hz, 1H, Ar-H), 7.41 (d, J=8.0 Hz, 1H, ArH), 7.24 (t, J=8.4 Hz, 1H, ArH), 6.98–6.85 (m, 4H, ArH), 4.50–4.42 (m, 1H, (S)-CH), 4.20–4.10 (m, 2H, =NCH$_2$), 3.86 (s, 3H, OCH$_3$), 3.09 (m, 4H), 2.91–2.8 (m, 3H), 2.71–2.55 (m, 3H), 2.65 (s, 3H, SCH$_3$); $^{13}$C NMR (CDCl$_3$) δ 154.90, 154.47, 152.82, 147.16, 141.82, 133.517, 126.35, 125.92, 125.72, 123.52, 121.56, 118.79, 117.67, 111.77, 60.42, 59.95, 57.08, 55.94, 54.51, 54.38, 51.16, 14.15; MS m/z 421 (M$^+$). Anal. Calcd. for C$_{23}$H$_{27}$N$_5$OS.0.5H$_2$O: C 64.16; H 6.55; N 16.27. Found C 64.37; H 6.49; N 16.25.

EXAMPLE 15
Preparation of (R)-(-)-3-[(4-(2-methoxyphenyl)piperazin-1-yl]methyl-5-methylthio-2,3-di-hydroimidazo[1,2-c] quinazoline The title compound was obtained in 71% yield using (R)-(-)-4-[(3-(4-methoxyphenyl)piperazine-1-yl)propan-2-ol-1-yl]amino-2-methylthioquinazoline by a similar procedure which described in Example 14: $[\alpha]_D^{26}$ −39.6 (c 4.7, CHCl$_3$); $^1$H NMR (CDCl$_3$) δ 7.96 (dd, J=1.4, 7.9 Hz, 1H, ArH), 7.52 (t, J=7.1 Hz, 1H, ArH), 7.41 (d, J=8.2 Hz, 1H, ArH), 7.24 (t, J=7.1 Hz, 1H, ArH), 7.03–6.85 (m, 4H, ArH), 4.50–4.42 (m, 1H, (S)-CH), 4.21–4.10 (m, 2H, =NCH$_2$), 3.86 (s, 3H, OCH$_3$), 3.09 (m, 4H), 2.91–2.8 (m, 3H), 2.71–2.55 (m, 2H), 2.65 (s, 3H, SCH$_3$), 2.59–2.55 (m, 1H); $^{13}$C NMR (CDCl$_3$) δ 154.90, 154.47, 152.82, 147.16, 141.83, 133.51, 126.35, 125.92, 125.71, 123.51 121.56, 118.78, 117.67, 111.75, 60.43, 59.99, 57.08, 55.94, 54.51, 51.16, 14.15; MS m/z 421 (M$^+$). Anal. Calcd. for C$_{23}$H$_{27}$N$_5$OS.0.5H$_2$O: C 64.16; H 6.55; N 16.27. Found C 64.45; H 6.54; N 15.94.

EXAMPLE 16
Preparation of (S)-(+)-3-[(4-(2-methoxyphenyl)piperazin-1-yl]methyl-5-methylthio-2,3-dihydroimidazo[1,2-c]quinazoline Procedure 2. To a stirred suspension of (S)-(+)-4-[(3-(4-methoxyphenyl)piperazine-1-yl)propan-2-ol-1-yl]amino-2-methylthioquinazoline (2.54 g, 5.57 mmol), potassium carbonate (2.31 g, 16.72 mmol) and triethylamine (2.33 mL, 16.72 mmol) in dry methylene chloride (170 mL) at +2° C. was dropwise added MsCl (0.56 mL, 7.25 mmol) over a period for 0.5 h. The mixture was stirred for 1 h at 2° C. and for 24 h at 25° C. It was washed with water (70 mL) and the aqueous layer was extracted with dichloromethane (50 mL). The combined organic extracts was dried over $Na_2SO_4$ (5 g) and evaporated to dryness. Acetonitrile (30 mL) was added to the residue and after stirring for 40 min the precipitate was collected by filtration to give 0.57 g (24%) of the racemic product: m.p. 173–174° C. Acetonitrile solution was evaporated, the residue was heated in vacuo (2 mm Hg, 50° C.) to give 1.80 g (75%, ee>98.5%) of the title compound as colorless solid foam.

EXAMPLE 17
Preparation of (R)-(–)-3-[(4-(2-methoxyphenyl)piperazin-1-yl]methyl-5-methylthio-2,3-dihydroimidazo[1,2-c]quinazoline The title compound was obtained in 72% yield using (R)-(–)-4-[(3-(4-methoxyphenyl)piperazine-1-yl)propan-2-ol-1-yl]amino-2-methylthioquinazoline as startung material by a similar procedure which described in Example 16.

EXAMPLE 18
Preparation of (S)-(–)-3-[(4-(2-Methoxyphenyl)piperazin-1-yl]methyl-2,3-dihydroimidazo[1,2-c]quinazolin-5(6H)-one.

The solution of (S)-(+)-3-[(4-(2-methoxyphenyl)piperazin-1-yl]methyl-5-methylthio-2,3-dihydroimidazo[1,2-c]quinazoline (1.2 g, 2.85 mmol) and NaOH (5.69 g, 142 mmol) in methanol (60 mL) and water (35 mL) was heated under reflux for 17 h. To a cooled solution was added c. HCl (6.0 mL, 68 mmol) and methanol was evaporated in vacuo. After addition of water (60 mL) the mixture was extracted with dichloromethane (3×60 mL). The organic solutions were dried over $Na_2SO_4$ (5g) and solvent was evaporated in vacuo. The residue was purified by column chromatography (eluent EtOAc:$CH_3OH$=10:1) to give 1.05 g (94.0%) of the title compound as colourless foam: $[\alpha]_D^{25}$ –33.0 (c 1.342, $CHCl_3$); $^1H$ NMR ($CDCl_3$) δ 9.65 (br s, 1H, NH), 7.97 (dd, 1H, J=9.2, 1.3 Hz, ArH), 7.47 (t, 1H, J=7.5 Hz, ArH), 7.13 (1H, t, J=7.2 Hz, ArH), 7.01–6.85 (m, 5H, ArH), 4.68–4.56 (m, 1H, (S)-CH), 4.25–4.09 (m, 2H, =NCH$_2$), 3.86 (s, 3H, OCH$_3$), 3.08–3.03 (m, 5H), 2.85–2.83 (m, 2H), 2.73–2.71 (m, 1H); $^{13}C$ NMR ($CDCl_3$) δ 154.02, 152.82, 150.29, 141.86, 139.60, 133.87, 126.91, 123.74, 123.49, 121.54, 118.78, 115.70, 112.72, 111.74, 60.51, 59.93, 55.92, 54.99, 54.62, 51.24; MS m/z 391 (M$^+$). Anal. Calcd. for $C_{22}H_{25}N_5O_2.H_2O$: C 64.53; H 6.65; N 17.10. Found C 64.40; H 6.59; N 17.0.

EXAMPLE 19
Preparation of (R)-(+)-3-[(4-(2-methoxyphenyl)piperazin-1-yl]methyl-2,3-dihydroimidazo[1,2-c]quinazolin-5(6H)-one The title compound was obtained in 98% yield from (R)-(–)-3-[(4-(2-methoxyphenyl)piperazin-1-yl]methyl-5-methylthio-2,3-dihydroimidazo[1,2-c]quinazoline using the similar procedure which described in Example 18. $[\alpha]_D^{25}$ +30.9 (c 3.178, $CHCl_3$); $^1H$ NMR ($CDCl_3$) δ 9.67 (br s, 1H, NH), 7.89 (d, 1H, J=8.8 Hz, ArH), 7.37 (t, 1H, J=7.7 Hz, ArH), 7.03 (1H, t, J=7.5 Hz, ArH), 6.91–6.75 (m, 5H, ArH), 4.54–4.49 (m, 1H, (S)-CH), 4.14–4.00 (m, 2H, =NCH$_2$), 3.86 (s, 3H, OCH$_3$), 3.00–2.94 (m, 5H), 2.82–2.75 (m, 2H), 2.73–2.71 (m, 1H), 2.51–2.46 (m, 1H); $^{13}C$ NMR ($CDCl_3$) δ 153.45, 152.23, 149.72, 141.26, 139.02, 133.29, 126.33, 123.15, 122.90, 120.96, 118.19, 115.12, 112.11, 111.18, 59.92, 59.31, 55.31, 54.40, 54.01, 50.63; MS m/z 391 (M$^+$). Anal. Calcd. for $C_{22}H_{25}N_5O_2.0.75H_2O$: C 65.19; H 6.72; N 17.29. Found C 65.31; H 6.48; N 17.34.

What is claimed is:

1. A (S)-(+)-3-substituted methyl-5-methylthio-2,3-dihydroimidazo[1,2-c]quinazoline compound having formula (S)-(+)-I:

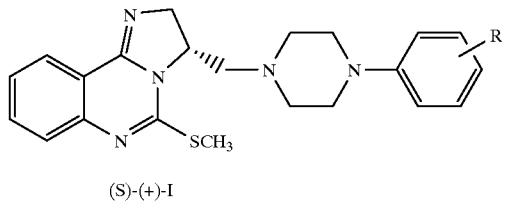

(S)-(+)-I wherein: R is halogen, hydrogen, methoxy, trifluormethyl, $C_1$–$C_4$ alkyl, nitro, acetyl, cyano or hydroxy group;
or pharmaceutically acceptable salts thereof.

2. A (S)-(–)-3-substituted methyl-2,3-dihydroimidazo[1,2-c]quinazolin-5(6H)-one compound having formula (S)-(–)-II:

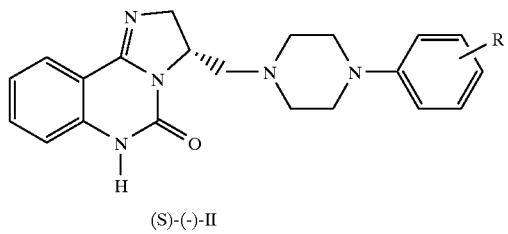

(S)-(-)-II wherein: R is halogen, hydrogen, methoxy, trifluoromethyl, $C_1$–$C_4$ alkyl, nitro, acetyl, cyano or hydroxy group;
or pharmaceutically acceptable salts thereof.

3. The imidazo[1,2-c]quinazoline compound according to claim 1, which is (S)-(+)-3-[4-[1-(2-methoxyphenyl)piperazinyl]]methyl-5-methylthio-2,3-dihydroimidazo[1,2-c]quinazolin-5(6H)-one.

4. The imidazo[1,2-quinazoline compound according to claim 2, which is (S)-(–)-3-[4-[1-(2-methoxyphenyl)piperazinyl]]methyl-2,3-dihydroimidazo[1,2-c]quinazolin-5(6H)-one.

5. A process for the preparation of (S)-(+)-3-substituted methyl-5-methylthio-2,3-dihydroimidazo[1,2-c]quinazoline compound having formula (S)-(+)-I:

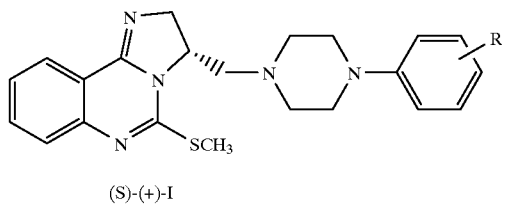

(S)-(+)-I wherein: R is halogen, hydrogen, methoxy, trifluoromethyl, $C_1$–$C_4$ alkyl, nitro, acetyl, cyano or hydroxy group; said process comprising the following steps:

a) reacting a compound of formula IV

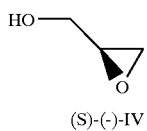
(S)-(-)-IV with phthalimidie using triphenylphosphine and azodicarboxylate to give a compound of formula V,

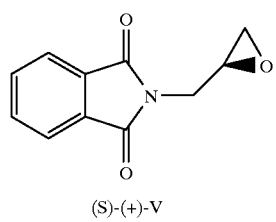
(S)-(+)-V b) reacting the resulting compound V with compound having a formula VI to yield a compound of formula VII,

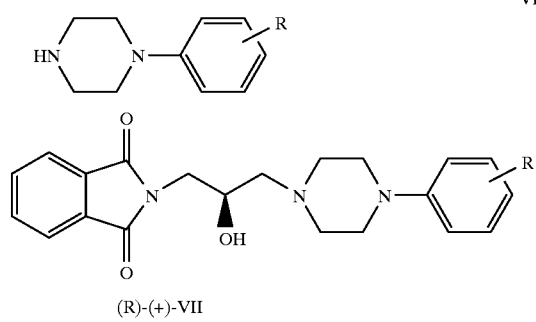
(R)-(+)-VII wherein R represents the same groups as defined above;

c) reacting the resulting compound VII with hydrazine to yield a compound of formula VIII,

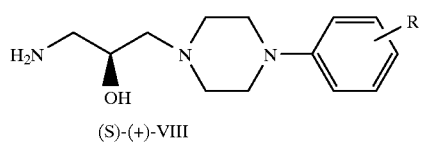
(S)-(+)-VIII wherein R represents the same groups as defined above;

d) treating the resulting compound VIII with either IX or X

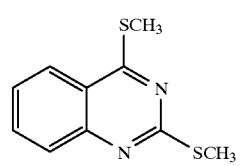
IX

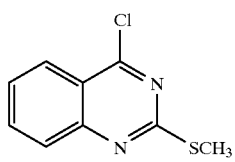
X to give a compound of formula XI; and

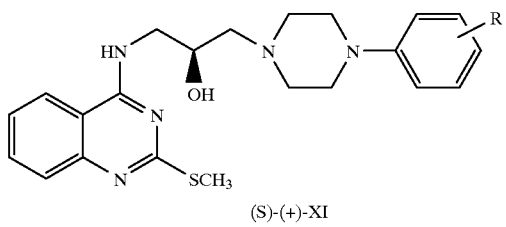
(S)-(+)-XI e) cyclizating the resulting compound XI to yield a compound of formula (S)-(+)-I.

6. A process for the preparation of (R)-(−)-3-substituted methyl-5-methylthio-2,3-dihydroimidazo[1,2-c]quinazoline compound having formula (R)-(−)-I:

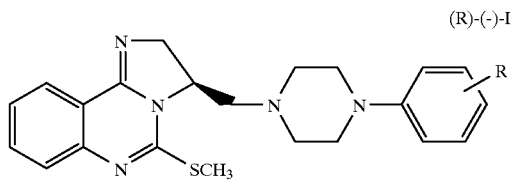
(R)-(−)-I wherein: R is halogen, hydrogen, methoxy, trifluoromethyl, $C_1$–$C_4$ alkyl, nitro, acetyl, cyano or hydroxy group; said process comprising the following steps:

a) reacting a compound of formula IV

(R)-(+)-IV with phthalimidie using triphenylphosphine and azodicarboxylate to give a compound of formula V,

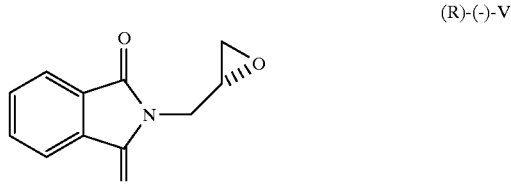
(R)-(−)-V b) reacting the resulting compound V with compound having a formula VI to yield a compound of formula VII,

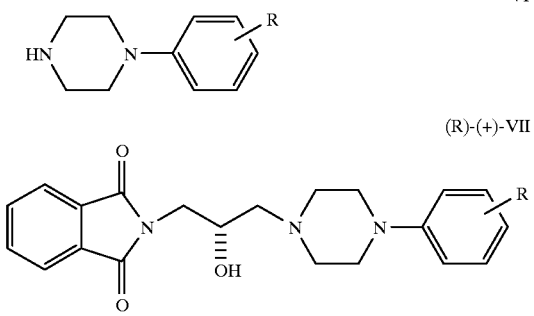

wherein R represents the same groups as defined above;

c) reacting the resulting compound VII with hydrazine to yield a compound of formula VIII,

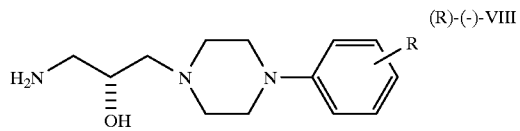

wherein R represents the same groups as defined above;

d) treating the resulting compound VIII with either IX or X to give a compound of formula XI; and

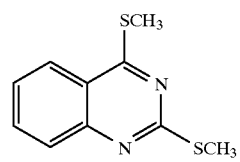

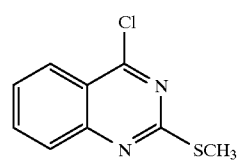

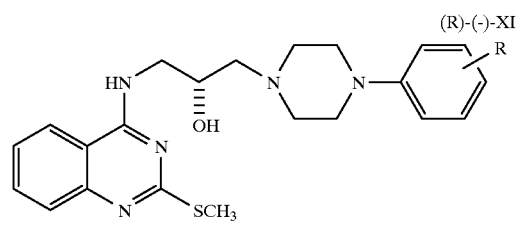

e) cyclizating the resulting compound XI to yield a compound of formula (R)-(−)-I.

7. A process for the preparation of (S)-(−)-3-substituted methyl-2,3-dihydroimidazo[1,2-c]quinazolin-5(6H)-one compound having formula (S)-(−)-II:

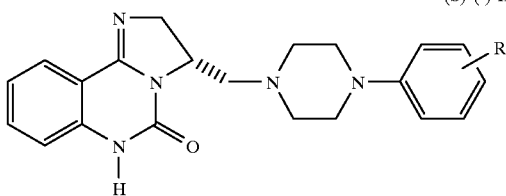

wherein: R is halogen, hydrogen, methoxy, trifluoromethyl, $C_1$–$C_4$ alkyl, nitro, acetyl, cyano or hydroxy group, said process comprising heating the compound (S)-(+)-I as set forth in claim 1 under acidic or basic condition.

8. A process for the preparation of (R)-(+)-3-substituted methyl-2,3-dihydroimidazo [1,2-c]quinazolin-5(6H)-one compound having formula (R)-(+)-II:

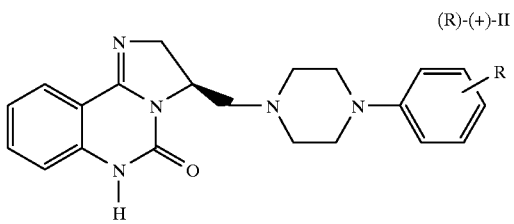

wherein: R is halogen, hydrogen, methoxy, trifluoromethyl, $C_1$–$C_4$ alkyl, nitro, acetyl, cyano or hydroxy group, said process comprising heating, under acidic or basic condition, the compound (R)-(−)-I having the formula:

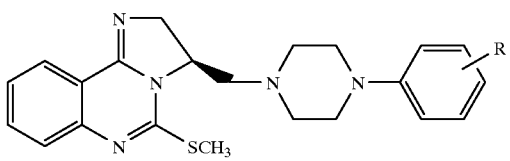

wherein: R is halogen, hydrogen, methoxy, trifluoromethyl, $C_1$–$C_4$ alkyl, nitro, acetyl, cyano or hydroxy group; or pharmaceutically acceptable salts thereof.

9. A pharmaceutical composition for the treatment of hypertension, which comprises a therapeutically effective amount of a compound of the formula (S)-(+)-I as set forth in claim 1 or a pharmaceutically acceptable salt thereof, as an active ingredient, in admixture with a pharmaceutically acceptable carrier or diluent for the active ingredient.

10. A pharmaceutical composition for the treatment of hypertension, which comprises a therapeutically effective amount of a compound of the formula (S)-(−)-II as set forth in claim 2 or a pharmaceutically acceptable salt thereof, as an active ingredient, in admixture with a pharmaceutically acceptable carrier or diluent for the active ingredient.

11. A pharmaceutical composition for the treatment of dysuria, which comprises a therapeutically effective amount of a compound of the formula (S)-(+)-I as set forth in claim 1 or a pharamaceutically acceptable salt thereof, as an active ingredient, in admixture with a pharmaceutically acceptable carrier or diluent for the active ingredient.

12. A pharmaceutical composition for the treatment of dysuria, which comprises a therapeutically effective amount of a compound of the formula (S)-(−)-II as set forth in claim 2 or a pharmaceutically acceptable salt thereof, as an active ingredient, in admixture with a pharmaceutically acceptable carrier or diluent for the active ingredient.

13. The pharmaceutical composition according to claim 9, wherein said compound is (S)-(+)-3-[4-[1-(2-methoxyphenyl)piperazinyl]]methyl-5-methylthio-2,3-dihydroimidazo[1,2-c]quinazolin-5(6H)-one.

14. The pharmaceutical composition according to claim 10, wherein said compound is (S)-(−)-3-[4-[1-(2-methoxyphenyl)piperazinyl]]methyl-2,3-dihydroimidazo[1,2-c]quinazolin-5(6H)-one.

15. The pharmaceutical composition according to claim 11, wherein said compound is (S)-(+)-3-[4-[1-(2-methoxyphenyl)piperazinyl]]methyl-5-methylthio-2,3-dihydroimidazo[1,2-c]quinazolin-5(6H)-one.

16. The pharmaceutical composition according to claim 12, wherein said compound is (S)-(−)-3-[4-[1-(2-methoxyphenyl)piperazinyl]]methyl-2,3-dihydroimidazo[1,2-c]quinazolin-5(6H)-one.

17. A method for the treatment of hypertension comprising administering a therapeutically effective amount of a compound of the formula (S)-(+)-I as set forth in claim 1 to a subject suffering from high blood pressure.

18. A method for the treatment of hypertension comprising administering a therapeutically effective amount of a compound of the formula (S)-(−)-II as set forth in claim 2 to a subject suffering from high blood pressure.

19. A method for the treatment of dysuria comprising administering a therapeutically effective amount of a compound of the formula (S)-(+)-I as set forth in claim 1 to a subject suffering from prostatauxe.

20. A method for the treatment of dysuria comprising administering a therapeutically effective amount of a compound of the formula (S)-(−)-II as set forth in claim 2 to a subject suffering from prostatauxe.

21. The method according to claim 17, wherein said compound is (S)-(+)-3-[4-[1-(2-methoxyphenyl)piperazinyl]]methyl-5-methylthio-2,3-dihydroimidazo[1,2-c]quinazolin-5(6H)-one.

22. The method according to claim 18, wherein said compound is (S)-(−)-3-[4-[1-(2-methoxyphenyl)piperazinyl]]methyl-2,3-dihydroimidazo[1,2-c]quinazolin-5(6H)-one.

23. The method according to claim 19, wherein said compound is (S)-(+)-3-[4-[1-(2-methoxyphenyl)piperazinyl]]methyl-5-methylthio-2,3-dihydroimidazo[1,2-c]quinazolin-5(6H)-one.

24. The method according to claim 20, wherein said compound is (S)-(−)-3-[4-[1-(2-methoxyphenyl)piperazinyl]]methyl-2,3-dihydroimidazo[1,2-c]quinazolin-5(6H)-one.

* * * * *

UNITED STATES PATENT AND TRADEMARK OFFICE
CERTIFICATE OF CORRECTION

PATENT NO. : 5,932,584
DATED : August 3, 1999
INVENTOR(S) : Ji-Wang Chern, et al.

It is certified that error appears in the above-identified patent and that said Letters Patent is hereby corrected as shown below:

Column 1, line 13 "dihydroinidazo" should be --dihydroimidazo--.

Column 5, line 36 "al-adrenoceptor" should be --$\alpha_1$-adrenoceptor--.

Signed and Sealed this

Twenty-third Day of May, 2000

Attest:

Q. TODD DICKINSON

*Attesting Officer*  *Director of Patents and Trademarks*